(12) United States Patent
Brahma et al.

(10) Patent No.: US 8,970,464 B2
(45) Date of Patent: Mar. 3, 2015

(54) SYSTEMS AND METHODS FOR MEASURING SHEET RESISTANCE

(75) Inventors: Kingsuk Brahma, San Francisco, CA (US); Saman Saeedi, Cupertino, CA (US); Sang Y. Youn, Cupertino, CA (US); Shafiq M Jamal, Pleasanton, CA (US); Taif A. Syed, Toronto (CA)

(73) Assignee: Appl Inc., Cupertino, CA (US)

( * ) Notice: Subject to any disclaimer, the term of this patent is extended or adjusted under 35 U.S.C. 154(b) by 208 days.

(21) Appl. No.: 13/601,762

(22) Filed: Aug. 31, 2012

(65) Prior Publication Data

US 2014/0062845 A1   Mar. 6, 2014

(51) Int. Cl.
  G09G 3/36 (2006.01)
  G01N 27/04 (2006.01)
  G06F 17/00 (2006.01)
  H01L 21/28 (2006.01)
  G09G 3/00 (2006.01)

(52) U.S. Cl.
  CPC ............. *G01N 27/045* (2013.01); *G06F 17/00* (2013.01); *G09G 3/36* (2013.01); *H01L 21/28* (2013.01); *G09G 3/006* (2013.01); *G09G 3/3611* (2013.01)
  USPC ................................. 345/98; 345/92; 702/65

(58) Field of Classification Search
  CPC ... G06F 3/038; G09G 5/00; G09G 2310/0264
  USPC .................. 345/76, 92, 98, 204, 205; 702/65
  See application file for complete search history.

(56) References Cited

U.S. PATENT DOCUMENTS

| | | | |
|---|---|---|---|
| 7,579,214 B2 | 8/2009 | Yamazaki et al. | |
| 7,791,193 B2 | 9/2010 | Singh et al. | |
| 8,004,508 B2 | 8/2011 | Kang et al. | |
| 2007/0080905 A1* | 4/2007 | Takahara | 345/76 |
| 2010/0271348 A1 | 10/2010 | Tsuchi | |
| 2012/0001874 A1* | 1/2012 | Kurokawa et al. | 345/175 |
| 2012/0139883 A1 | 6/2012 | Lee et al. | |

* cited by examiner

*Primary Examiner* — Joe H Cheng
(74) *Attorney, Agent, or Firm* — Fletcher Yoder PC (57) ABSTRACT

The present disclosure is directed to systems and methods for determining sheet resistance values in a liquid crystal display (LCD) panel. In certain embodiments, a system for determining sheet resistance values in an LCD panel may include a display driver integrated circuit (IC). The display driver IC may include a first switch coupled to a first input/output (I/O) pad and a second I/O pad such that the first I/O pad is configured to couple to a voltage source and the second I/O pad is configured to couple to a current source. The display driver IC may also include a second switch coupled to a third I/O pad and the second I/O pad such that the second switch has substantially the same geometry as the first switch and the third I/O pad is configured to couple to a thin-film transistor (TFT) layer of the display panel.

20 Claims, 9 Drawing Sheets

SYSTEMS AND METHODS FOR MEASURING SHEET RESISTANCE

BACKGROUND

The present disclosure relates generally to measuring sheet resistances of semiconductor devices and, more specifically, to measuring a sheet resistance from within a semiconductor device.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Semiconductor devices are found in nearly all modern electronics. Indeed, semiconductors are used in processors, memory devices, and even electronic displays. For example, liquid crystal display (LCD) panels use thin-film transistors (TFTs) to activate and deactivate pixels to program the LCD panel. Various components of the LCD panel propagate the signals that program the LCD panel. The sheet resistance of such components may impact the operation of the LCD panel. For example, sheet resistance may correspond to a quality of the LCD panel; a sheet resistance outside a defined range may indicate that the LCD panel may fail to operate as designed.

As a result, sheet resistances are often tested when LCD panels are manufactured. Manufacturers generally sample sheet resistances of a wafer on which many separate display panels have been formed. Using the sampled sheet resistance values, manufacturers may then estimate the sheet resistance for each display panel constructed from the single wafer. The sheet resistance, however, may vary at different locations on the wafer. As such, the manufacturers' estimates regarding the sheet resistance for its manufactured display panels may not be accurate. Moreover, it is difficult to measure sheet resistance after the display has been manufactured and placed within an electronic device.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure generally relates to monitoring a sheet resistance of a layer in a display panel on which thin-film transistors (TFTs) may be formed (i.e., TFT layer). The sheet resistance may provide valuable information concerning the quality of a manufacturing process used to create the display panel. For instance, the sheet resistance may provide an indication of an open circuit condition, whether a slew rate for the TFT will be too high or too low, and so forth.

In certain embodiments, a display driver integrated circuit (IC) may be a chip-on-glass (COG) circuit that may include a number of electrical paths coupled to a number of conductive layers of the display panel. The display driver IC may also include another number of electrical paths, which may not be coupled to a conductive layer. In general, one of the conductive layers coupled to the display driver IC may be a TFT layer. To determine the resistance of the TFT layer, a controller may first determine a resistance of a first electrical path within the display driver IC that may not be coupled to the TFT layer. Using the resistance of the first electrical path, which may be substantially similar to the other electrical paths within the display driver IC, the controller may determine the sheet resistance of the TFT layer.

For instance, in one embodiment, the display driver IC may include a number of semiconductor switches coupled to a number of input/output (I/O) pads on the COG circuit. One of the semiconductor switches may be coupled to an external voltage source (i.e., external from the display driver IC) via one I/O COG pad and each of the remaining semiconductor switches may be coupled to a distinct conductive layer via other I/O COG pads. That is, each of the remaining semiconductor switches of the display driver IC may be coupled to a respective COG pad that may be coupled to a respective conductive layer. In addition to being connected to a conductive (e.g., TFT) layer or an external voltage source, each switch may be coupled to a common node located at another COG pad, which may be coupled to a pad on a flex on glass (FOG) circuit. The FOG pad may then be coupled to a direct current (DC) source. Using this circuitry, a process may be undertaken to determine the resistance of a TFT layer coupled to a COG pad.

As mentioned above, to determine the resistance of one particular TFT layer coupled to one of the COG pads, a controller may first determine a resistance of a first electrical path within the display driver IC that may not be coupled to the TFT layer. For example, the controller may close a first switch in the display driver IC such that the first switch may be coupled to the external voltage source. At the same time, the controller may open the remaining switches in the display driver IC such that the FOG pad is directly coupled to the external voltage source via the first switch. The controller may then measure a floating voltage value ($V_i$) at the FOG pad due to the external voltage source. The controller may then apply a DC current through the first switch using the DC current source. As the DC current conducts through the first switch, the resistance within the first switch may cause the voltage at the FOG pad to drop from its initial voltage value ($V_i$). The controller may then measure a new floating voltage value ($V'_i$) (i.e., reference voltage value), which may account for the voltage drop due to the resistance in the first switch when the DC current conducts through the first switch. Using the difference between the initial voltage value ($V_i$) and the reference voltage value ($V'_i$) and the amount of DC current ($I_{test}$) provided by the DC current source, the controller may determine the resistance of the path ($R_{path}$) through the first switch.

After determining the resistance of the path ($R_{path}$), which may be substantially similar to the other electrical paths within the display driver IC, the controller may determine the resistance of each TFT layer coupled to the COG pads. That is, the controller may open the first switch and close a second switch, which may be coupled to a TFT layer. The controller may then sweep the DC current source until the floating voltage value ($V_x$) at the FOG pad is substantially equal to the reference voltage value ($V'_i$). When the floating voltage value ($V_x$) is substantially equal to the reference voltage value ($V_i$) the second switch may be biased such that it has a resistance substantially equal to the resistance ($R_{path}$) of the first switch. The controller may then use the DC current value ($I_{test\_x}$) that caused the floating voltage value ($V_x$) at the FOG pad to be substantially equal to the reference voltage value ($V'_i$) to determine the resistance of the TFT layer coupled to the second switch. For instance, the controller may determine the resistance of the TFT layer based on the reference voltage value ($V'_i$), the DC current value ($I_{test\_x}$) that corresponds to when the floating voltage value ($V_x$) at the FOG pad to be substantially equal to the floating voltage value ($V'_t$), and the resistance ($R_{path}$) of the second switch.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION OF SPECIFIC EMBODIMENTS

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is directed to systems and methods for determining sheet resistance values in a liquid crystal display (LCD) panel. In certain embodiments, a test circuit may be coupled to a pad on a flex-on-glass (FOG) circuit, which may be coupled to a display driver integrated circuit (IC), to measure the sheet resistance of a TFT layer in the LCD panel. The display driver IC may include a number of switches. Some of the switches may be coupled to an external voltage source or different conductive layers in the LCD panel. The test circuit may include a controller that may use one of the switches in the display driver IC to determine a common reference voltage and a common resistance value for each switch in the display driver IC. The controller may then send a signal to the test circuit to bias each of the other switches to the common reference voltage using a direct current (DC) current provided by a current source in the test circuit. By biasing the switches in the display driver IC to the common reference voltage, the controller may treat each switch in the display driver IC as having substantially similar resistance values. As a result, the controller may determine the sheet resistance of a TFT layer coupled to one of the switches in the display driver IC based at least in part on the DC current provided to the switch, the common reference voltage, and the resistance value of each switch in the display driver IC. Additional details with regard to how the test circuit may determine the sheet resistance values of the LCD panel will be discussed below with reference to FIGS. 1-7.

Figure 1:
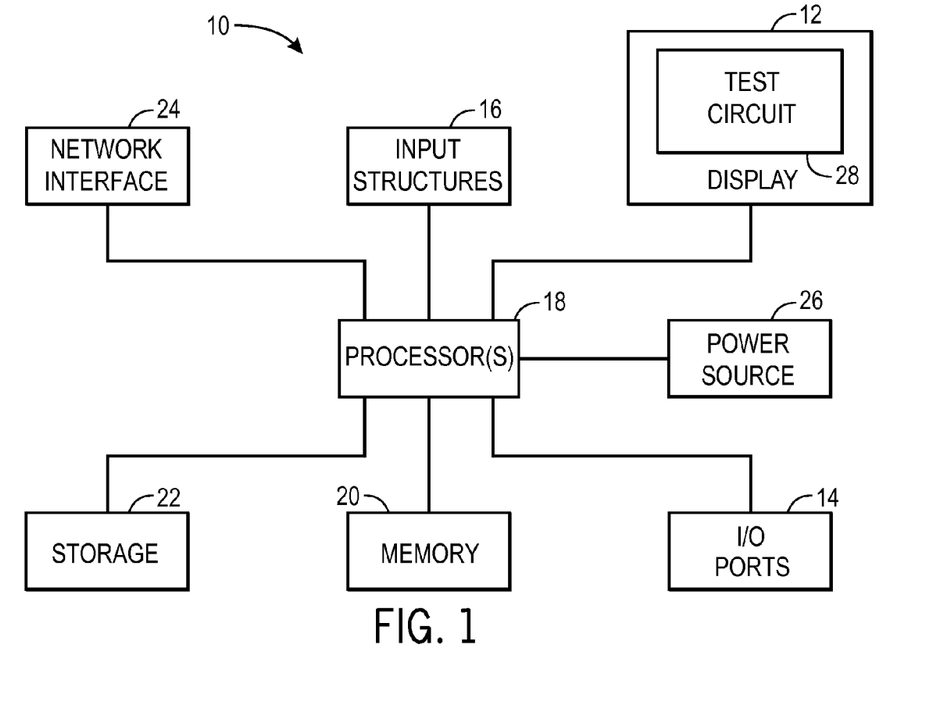
FIG. 1 is a block diagram of exemplary components of an electronic device, in accordance with an embodiment.

A variety of electronic devices may incorporate systems and methods for determining the sheet resistance values of an LCD panel. FIG. 1 represents a block diagram of such an electronic device 10. The various functional blocks shown in FIG. 1 may include hardware elements (including circuitry), software elements (including computer code stored on a computer-readable medium), or a combination of both hardware and software elements. It should be further be noted that FIG. 1 is merely one example of a particular implementation and is intended to illustrate the types of components that may be present in the electronic device 10. For example, in the presently illustrated embodiment, these components may include a display 12, I/O ports 14, input structures 16, one or more processors 18, a memory device 20, a non-volatile storage 22, a networking device 24, a power source 26, a sheet resistance test circuit 28, and the like.

With regard to each of these components, the display 12 may be used to display various images generated by the electronic device 10. Moreover, the display 12 may be a touch-screen liquid crystal display (LCD), for example, which may enable users to interact with a user interface of the electronic device 10. In some embodiments, the display 12 may be a MultiTouch™ display that can detect multiple touches at once. The I/O ports 14 may include ports configured to connect to a variety of external I/O devices. The input structures 16 may include the various devices, circuitry, and pathways by which user input or feedback is provided to the processor 18.

The processor(s) 18 may provide the processing capability to execute the operating system, programs, user and application interfaces, and any other functions of the electronic device 10. The instructions or data to be processed by the processor(s) 18 may be stored in a computer-readable medium, such as the memory 20. The memory 20 may be provided as a volatile memory, such as random access memory (RAM), and/or as a non-volatile memory, such as read-only memory (ROM). The components may further include other forms of computer-readable media, such as the non-volatile storage 22, for persistent storage of data and/or instructions. The non-volatile storage 22 may include flash memory, a hard drive, or any other optical, magnetic, and/or solid-state storage media. The non-volatile storage 22 may be used to store firmware, data files, software, wireless connection information, and any other suitable data. In certain embodiments, the processor 18 may control hardware components located within the electronic device 10, including the display 12 and the test circuit 28.

The network device 24 may include a network controller or a network interface card (NIC). Additionally, the network device 24 may be a Wi-Fi device, a radio frequency device, a Bluetooth® device, a cellular communication device, or the like. The network device 24 may allow the electronic device 10 to communicate over a network, such as a Local Area Network (LAN), Wide Area Network (WAN), or the Internet. The power source 26 may include a variety of power types such as a battery or AC power.

The test circuit 28 may include control logic and various circuitries to determine the sheet resistance of one or more conductive layers in the display 12. Additional details with regard to how the test circuit 28 may be used to determine the sheet resistance are discussed below with reference to FIGS. 4-7.

Figure 2:
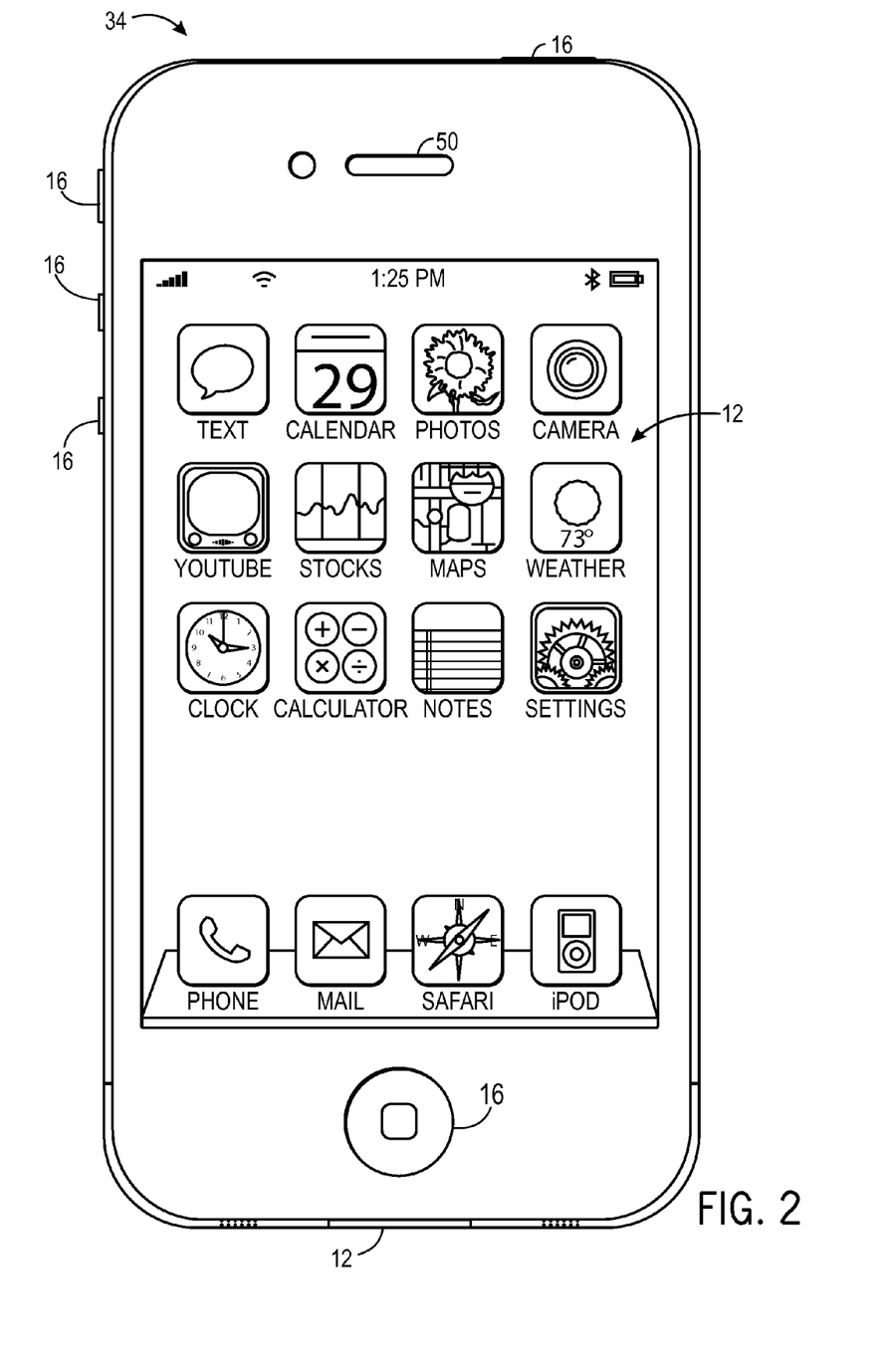
FIG. 2 is a front view of a handheld electronic device, in accordance with an embodiment.

With the foregoing in mind, FIG. 2 illustrates an electronic device 10 in the form of a handheld device 34. FIG. 2 illustrates a cellular telephone, but it should be noted that while the depicted handheld device 34 is provided in the context of a cellular telephone, other types of handheld devices (such as media players for playing music and/or video, personal data organizers, handheld game platforms, and/or combinations of such devices) may also be suitably provided as the electronic device 10. As discussed with respect to the general electronic device 10 of FIG. 1, the handheld device 34 may allow a user to connect to and communicate through the Internet or through other networks, such as local or wide area networks. The handheld electronic device 34 may also communicate with other devices using short-range connections, such as Bluetooth® and near field communication. By way of example, the handheld device 34 may be a model of an iPod®, or iPhone® available from Apple Inc. of Cupertino, Calif.

The handheld device 34 may include an enclosure or body that protects the interior components from physical damage and shields them from electromagnetic interference. The enclosure may be formed from any suitable material such as plastic, metal or a composite material and may allow certain frequencies of electromagnetic radiation to pass through to wireless communication circuitry within the handheld device 34 to facilitate wireless communication. In the depicted embodiment, the enclosure includes user input structures 16 through which a user may interface with the device. Each user input structure 16 may be configured to help control a device function when actuated.

In the depicted embodiment, the handheld device 34 and the tablet device 40 include the display 12. The display 12 may be a touch-screen LCD used to display a graphical user interface (GUI) that allows a user to interact with the handheld device 34. The handheld electronic device 34 also may include various input and output (I/O) ports that allow connection of the handheld device 34 to external devices.

Figure 3:
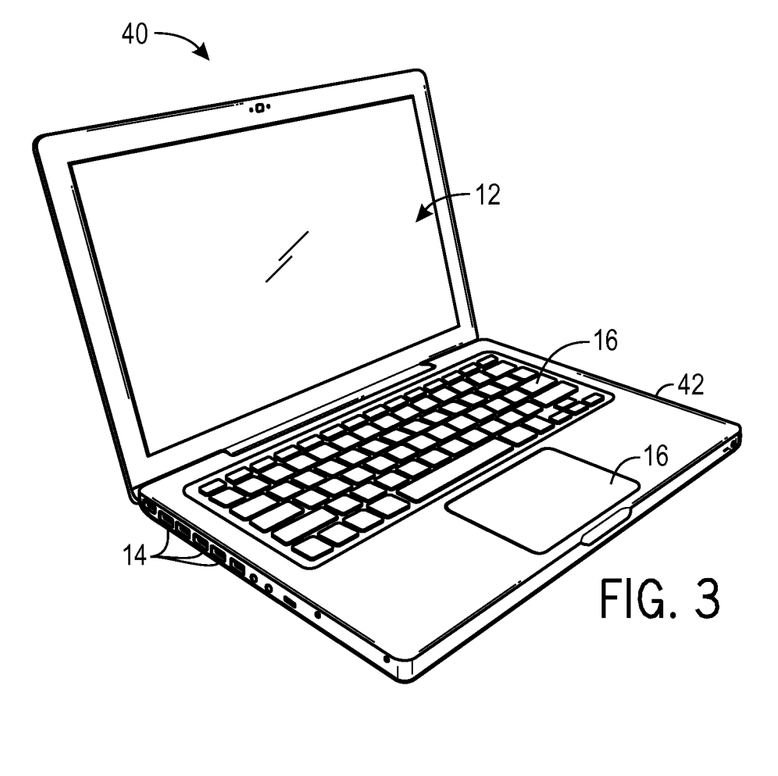
FIG. 3 is a view of a computer, in accordance with an embodiment.

In addition to handheld device 34, the electronic device 10 may also take the form of a computer or other type of electronic device. Such computers may include computers that are generally portable (such as laptop, notebook, and tablet computers) as well as computers that are generally used in one place (such as conventional desktop computers, workstations, and/or servers). In certain embodiments, the electronic device 10 in the form of a computer may be a model of a MacBook®, MacBook® Pro, MacBook Air®, iMac®, Mac® mini, iPad® or Mac Pro® available from Apple Inc. By way of example, an electronic device 10 in the form of a laptop computer 40 is illustrated in FIG. 3 in accordance with one embodiment. The depicted computer 40 includes a housing 42, a display 12, input structures 16, and input/output ports 14.

In one embodiment, the input structures 16 (such as a keyboard and/or touchpad) may be used to interact with the computer 40, such as to start, control, or operate a GUI or applications running on the computer 40. For example, a keyboard and/or touchpad may allow a user to navigate a user interface or application interface displayed on the display 12.

As depicted, the electronic device 10 in the form of the computer 40 may also include various input and output ports 14 to allow connection of additional devices. For example, the computer 40 may include an I/O port 14, such as a USB port or other port, suitable for connecting to another electronic device, a projector, a supplemental display, and so forth. The computer 40 may include network connectivity, memory, and storage capabilities, as described with respect to FIG. 1. As a result, the computer 40 may store and execute a GUI and other applications.

Figure 4:
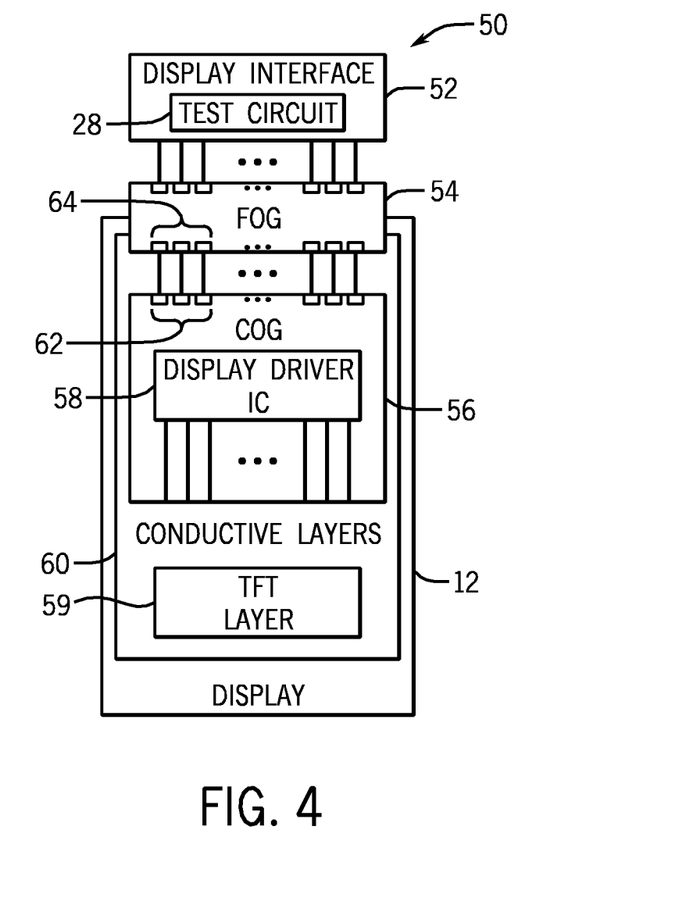
FIG. 4 is a block diagram of a display in the electronic device of FIG. 1, in accordance with an embodiment.

With the foregoing discussion in mind, FIG. 4 depicts a block diagram 50 of the display 12 in the electronic device 10. As shown in FIG. 4, the display 12 includes a display interface 52, a flex-on-glass (FOG) circuit 54, a chip-on-glass (COG) circuit 56 that may include a display driver integrated circuit (IC) 58, and a thin-film transistor (TFT) layer 59 that may be part of one or more conductive layers 60. The COG circuit 56 may include the display driver IC 58, which may be used to determine the resistance of the TFT layer 59. The TFT layer 59 may include a layer of the display 12 on which TFTs may be disposed. In one embodiment, the display driver IC 58 may be coupled to one or more conductive layers 60 and to the FOG circuit 54 via input/output (I/O) pads 62 on the COG circuit 56.

The FOG circuit 54 is a flexible printed circuit (FPC) that may be coupled to the display interface 52, the COG circuit 56, and the TFT layer 59. Like the COG circuit 56, the FOG circuit 54 may include I/O pads 64. The I/O pads 64 in the FOG circuit 54 may be coupled to I/O pads 62 on the COG circuit 56 and to the test circuit 28 on the display interface 52.

The display interface 52 may include various circuitry to control the display 12. For instance, as mentioned above, the display interface 52 may include the test circuit 28, which may be used to determine the resistance of the TFT layer 59. The test circuit 28 may include control logic that may enable the test circuit 28 to determine values that allow the processor 18 to determine the resistance of the TFT layer 59. In certain embodiments, the control logic of the test circuit 28 may be coupled to the display driver IC 58 such that it may control various components (e.g., switches) within the display driver IC 58 to determine the resistance of the TFT layer 59. However, it should be noted that, in other embodiments, the processor 18 or the like may be used to control various components (e.g., switches) within the display driver IC 58 and the test circuit 28. Additional details with regard to one embodiment of the interconnections between the test circuit 28, the FOG circuit 54, and the display driver IC 58 are provided below.

Figure 5A:
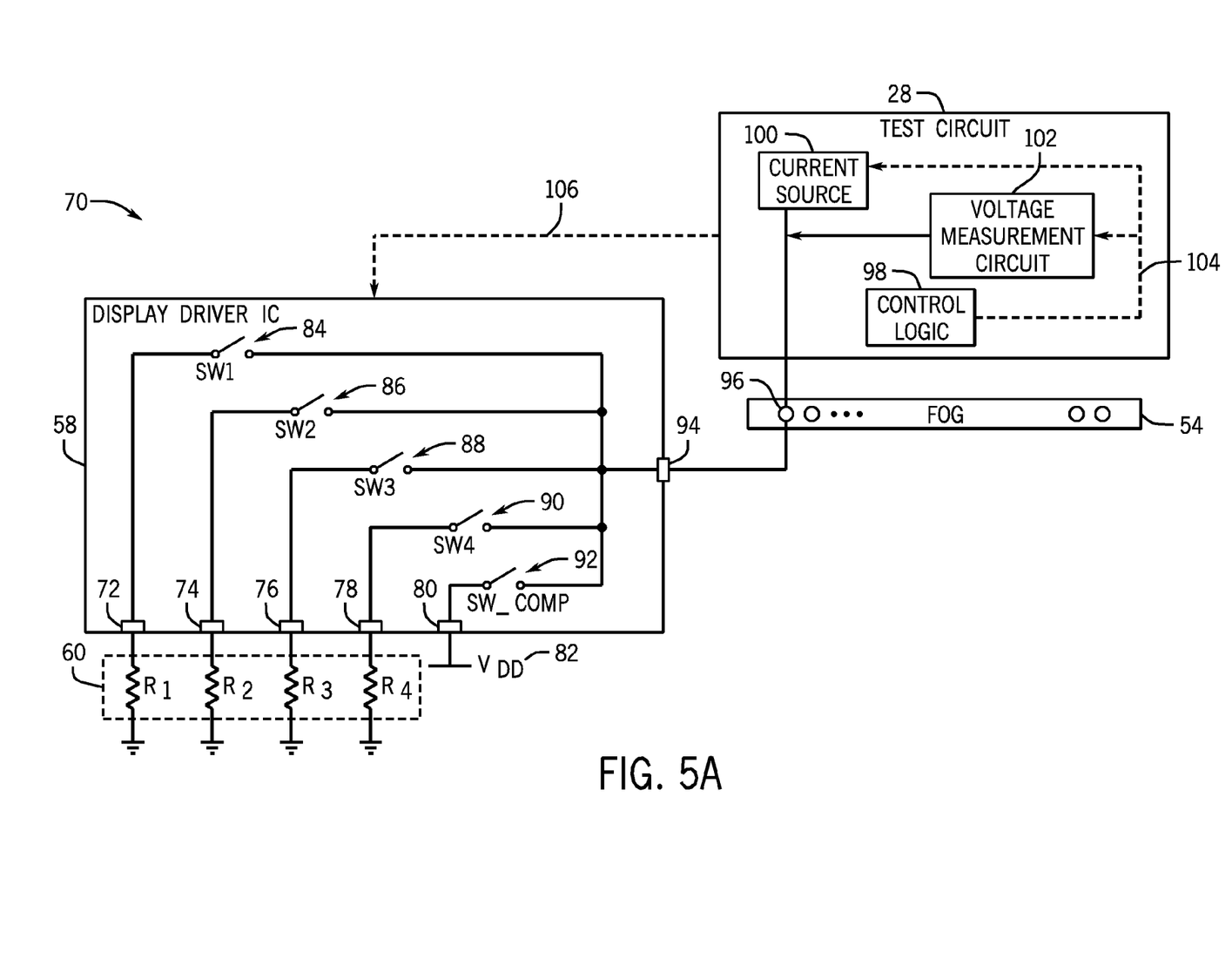
FIGS. 5A-5D are block diagrams of a display driver integrated circuit (IC) in the display of FIG. 4, in accordance with an embodiment.

Referring now to FIG. 5A, a block diagram 70 represents circuitry to test various resistance of the TFT layer 59. As mentioned above, the display driver IC 58 may be coupled to the TFT layer 59 via COG pads 72, 74, 76, 78. In one embodiment, each of the COG pads 72, 74, 76, 78 may be coupled to a different TFT layer. As such, a resistance (i.e., $R_1$, $R_2$, $R_3$, $R_4$) of each respective TFT layer may be different. In addition to being coupled to the TFT layer 59, the display driver IC 58 may include a COG pad 80 that may be coupled to an external voltage source 82 ($V_{DD}$). The external voltage source 82 ($V_{DD}$) may be a voltage source external to the display driver IC 58. In one embodiment, the external voltage source 82 ($V_{DD}$) may be provided by the display 12 or by another component within the electronic device 10.

Each COG pad described above 72, 74, 76, 78, 80 may also be coupled to a respective switch 84, 86, 88, 90, 92 such that each respective switch 84, 86, 88, 90, 92 may be coupled to a common node located at a common COG pad 94. Each switch 84, 86, 88, 90, 92 may be a semiconductor switch such as a metal-oxide-semiconductor field-effect transistor (MOSFET) or the like. In one embodiment, each switch 84, 86, 88, 90, 92 may be substantially similar in geometry such that they each have similar electrical characteristics (e.g., operating resistance).

The FOG circuit 54 may include a FOG pad 96 that be coupled to each switch 84, 86, 88, 90, 92 via the common COG pad 94. The FOG pad 96 may also be coupled to the test circuit 28. The test circuit 28 may include control logic 98 (e.g., controller), a current source 100, and a voltage measurement circuit 102. The control logic 98 may be a microprocessor or some other hardware logic governed by control signals from the processor(s) 18 described above. In one embodiment, the control logic 98 may communicate with the current source 100 and the voltage measurement circuit 102 via communication path 104. As such, the control logic 98 may control the amount of current conducting from the current source 100 and measure a floating voltage of the FOG pad 96 using the voltage measurement circuit 102. Moreover, the control logic 98 may also control the operation of each switch 84, 86, 88, 90, 92 in the display driver IC 58 via a communication path 106. By measuring the floating voltage at the FOG pad 96, controlling the DC current provided to each switch 84, 86, 88, 90, 92, and controlling the operation of each switch 84, 86, 88, 90, 92, the control logic 98 may determine the resistance of the TFT layer 59.

Figure 6:
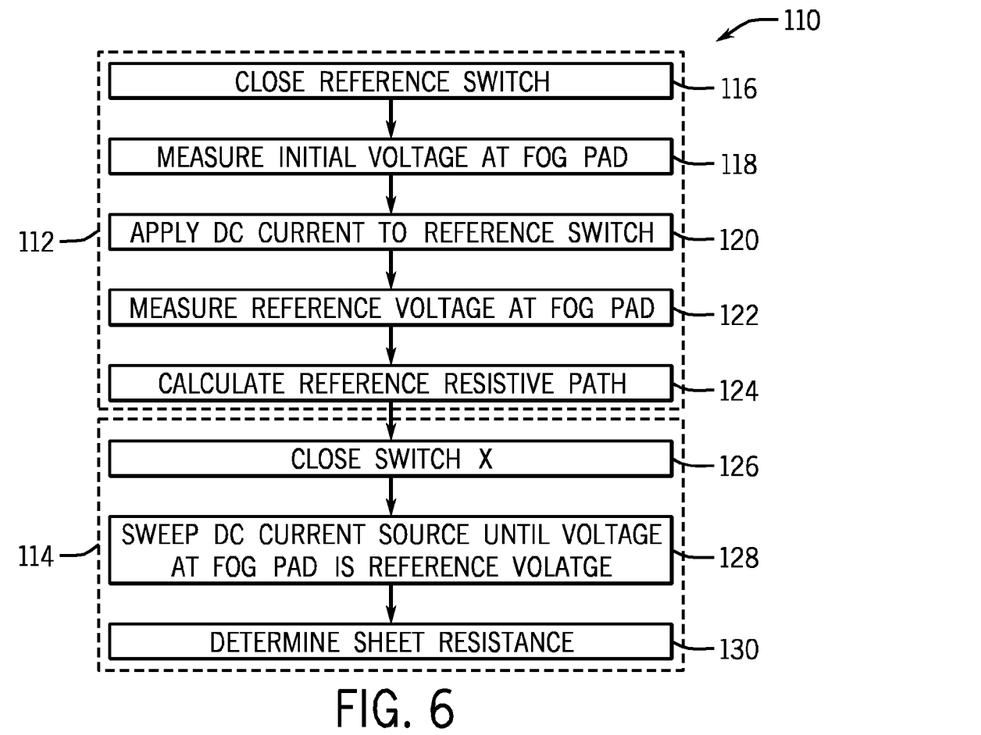
FIG. 6 depicts a flow chart of a method for determining a sheet resistance value using circuitry in the display driver IC of FIGS. 5A-5D, in accordance with an embodiment.

Keeping the foregoing in mind, FIG. 6 depicts a flow chart 110 of a method for determining the resistance of the TFT layer 59. Generally, at block 112, the control logic 98 may obtain voltage measurements via the voltage measurement circuit 102 to determine a resistance value for a resistance path between the COG pad 80 and the COG pad 94 via the switch 92 using the external voltage source 82 ($V_{DD}$) and the current source 100. At block 114, the control logic 98 may use the resistance value for the resistance path between the COG pad 80 and the COG pad 94 via the switch 92 to determine the resistance of the TFT layer 59 coupled to one of the switches 84, 86, 88, 90.

Figure 5B:
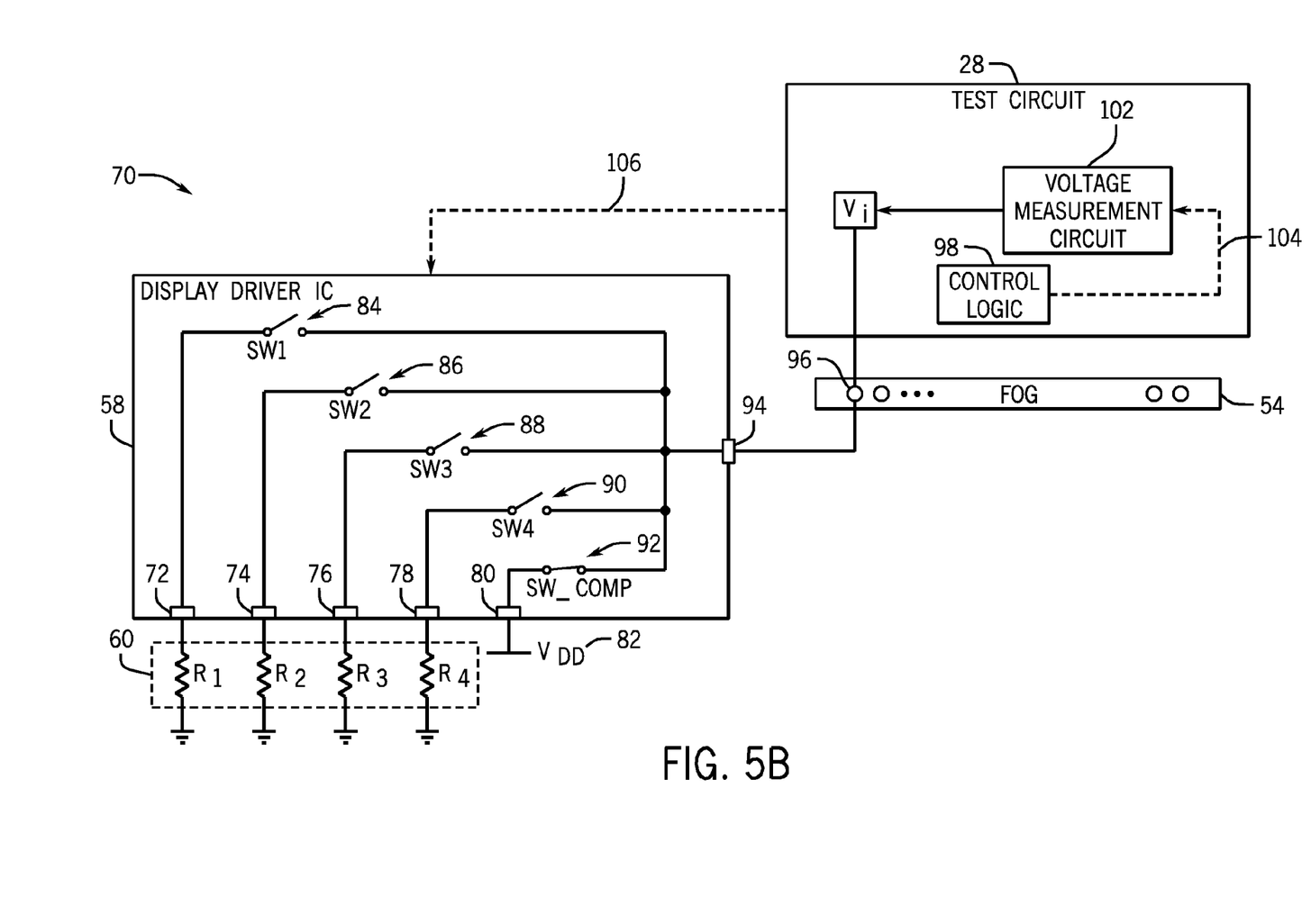
Figure 5C:
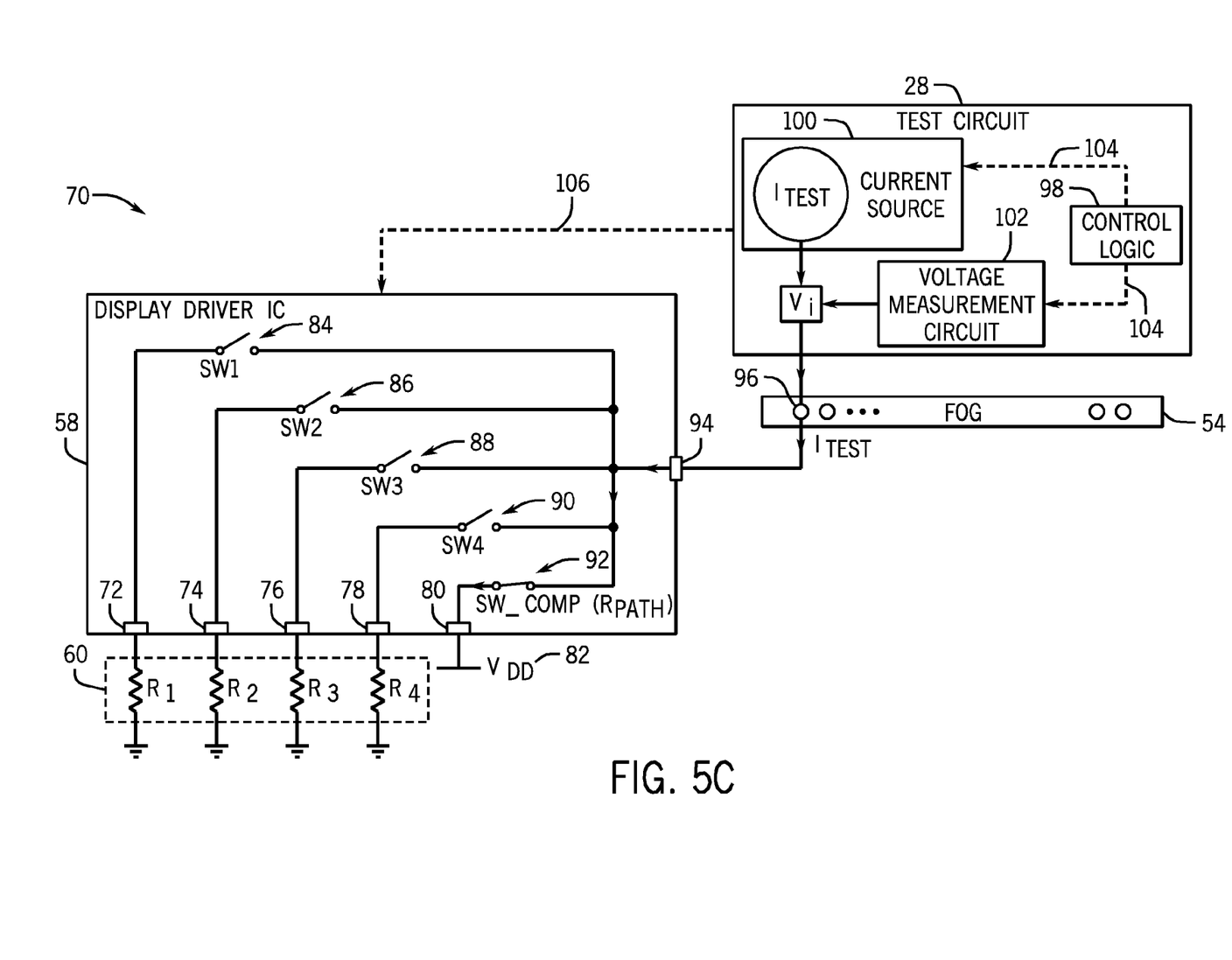

Referring to block 112 and FIG. 5B, to determine the resistance value for the resistance path through the switch 92, the control logic 98 may, at block 116, send a signal to the reference switch 92 to close, thereby coupling the FOG pad 94 to the external voltage source ($V_{DD}$) 82. At block 118, the control logic 98 may receive a measurement of an initial floating voltage value ($V_i$) at the FOG pad 96 from the voltage measurement circuit 104. While the reference switch 92 is still closed, the control logic 98 may, at block 120, send a signal to the current source 100 to provide a direct current (DC) current ($I_{test}$) to the FOG pad 96 (FIG. 5C). At block 122, the control logic 98 may again measure the floating voltage at the FOG pad 96, which may be referred to as a reference voltage ($V'_i$). Using the initial floating voltage value ($V_i$), the reference voltage ($V'_i$), and the DC current value ($I_{test}$) provided to the FOG pad 96, at block 124, the control logic 98 may calculate a resistance value ($R_{path}$) for the resistance path between the COG pad 80 and the COG pad 94 via the switch 92 according to Equation 1.

$$R_{path}=(V'_i-V_i)/I_{test} \quad (1)$$

As such, the control logic 98 may determine the resistance of the reference switch 92 when biased with the reference voltage ($V'_i$). Keeping this in mind, since each switch 84, 86, 88, 90, 92 in the display driver IC 58 has substantially the same geometry, each switch 84, 86, 88, 90 may be biased with the reference voltage ($V'_i$) such that the resistance value of each switch 84, 86, 88, 90 may be similar to the resistance value of the reference switch 92 ($R_{path}$). That is, the gate-to-source voltage of each switch 84, 86, 88, 90 may be biased with the reference voltage ($V'_i$) such that each switch 84, 86, 88, 90 may exhibit the same electrical resistance properties. As such, referring to FIG. 5D, to bias the switch 84, for example, such that the resistance value of the switch 84 may be substantially the same as the resistance value of the reference switch 92 ($R_{path}$), at block 126, the control logic 98 may close the switch 84 and open the reference switch 92.

Figure 5D:
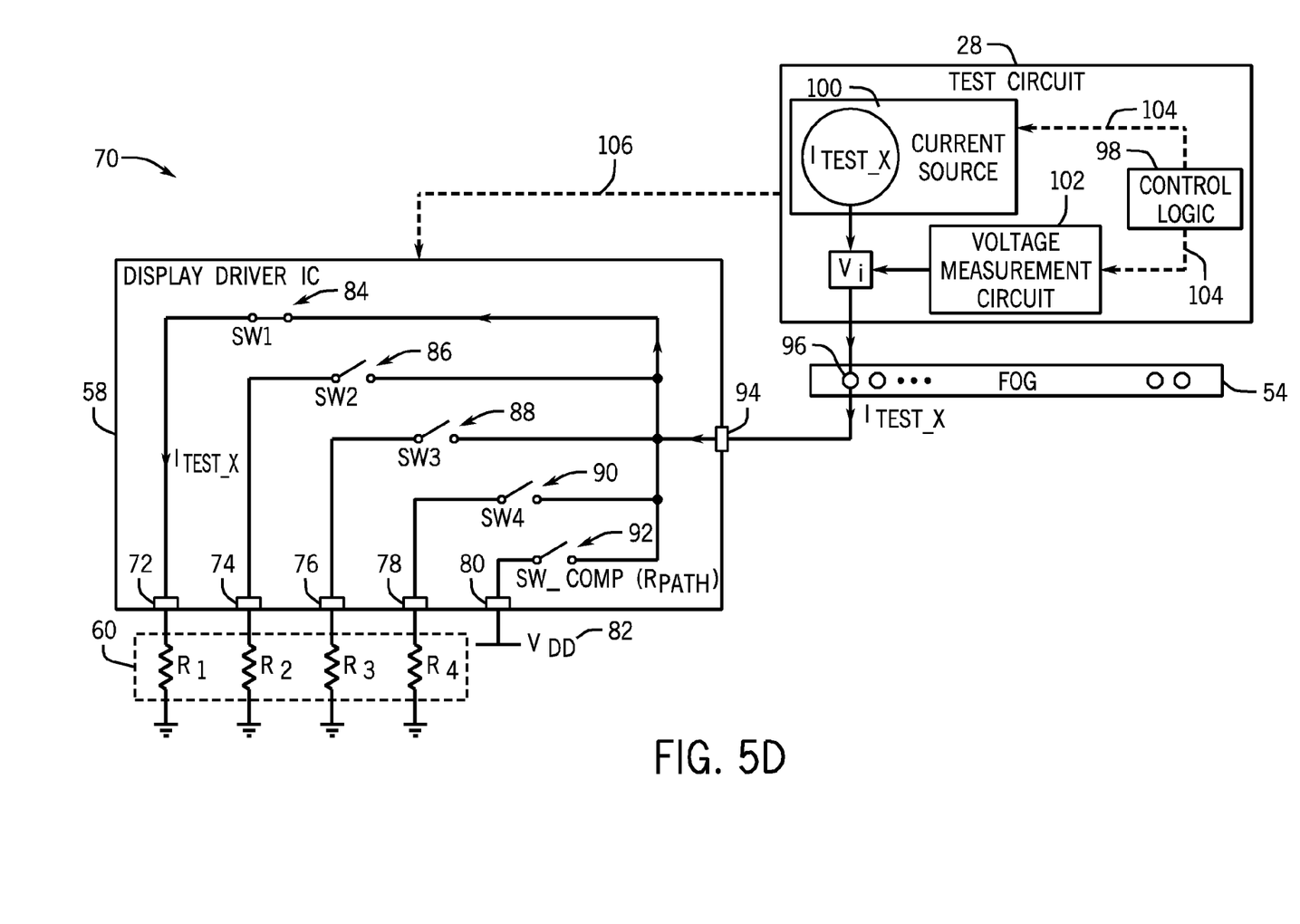

At block 128, the control logic 98 may sweep the current source 100 until the floating voltage at the FOG pad 96 is substantially the same as the reference voltage ($V'_i$). As such, the control logic 98 may supply a number of different currents to the FOG pad 96 and simultaneously monitor the floating voltage values of the FOG pad 96. When the floating voltage value at the FOG pad 96 is substantially similar to the reference voltage ($V'_i$), the control logic 98 may determine that the switch 84 is biased in the same manner as the reference switch 92. That is, the switch 84 may be biased like the reference switch 92 when the current source 100 reaches some value ($I_{test\_x}$). As a result, the switch 84 may have substantially the same resistance ($R_{path}$) as the reference switch 92.

Since the resistance of the switch 84 may be substantially the same resistance ($R_{path}$) as the reference switch 92, at block 130, the control logic 98 may determine the sheet resistance ($R_1$) of the TFT layer 59 coupled to the switch 84. That is, the resistance ($R_x$) of a respective conductive layer coupled to a switch X may be determined based on Equation 2.

$$R_x=(V_x-I_{test\_x}*R_{path})I_{test\_x} \quad (2)$$

By solving Equation 2, the control logic 98 may assume that the difference between the current $I_{test}$ used for the switch 92 and the current $I_{test\_x}$ used for any switch 84, 86, 88, or 80 may be small enough such that the switch 84, 86, 88, or 80 may remain in deep triode region of operation. As such, the resistance of the switch 92 and the switch 84, 86, 88, or 80 may be substantially similar when biased using the same voltage ($V'_i$).

Although the method 110 has been described as being performed by the control logic 98, it should be noted that, in some embodiments, the method 110 may be performed by the processor 18 or the like. For example, the test circuit 28 may be invoked by the processor 18 to perform the method 110 described above.

Figure 7:
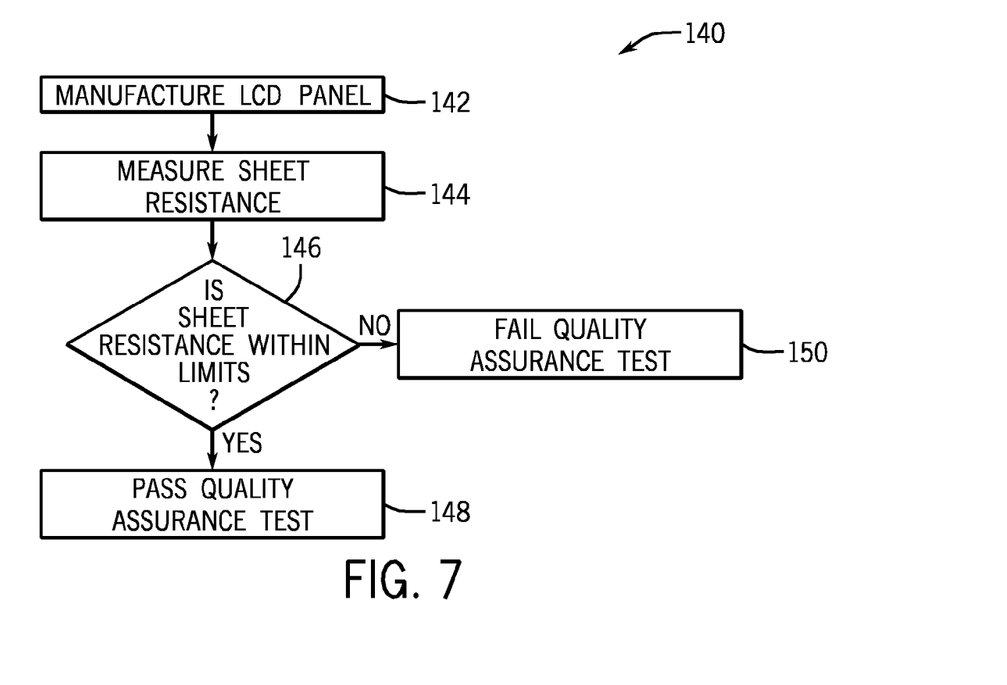
FIG. 7 depicts a flow chart of a method for performing quality control in a manufacturing process for the display of FIG. 4, in accordance with an embodiment.

After determining the resistance ($R_1$) of the TFT layer 59 coupled to the switch 84, the control logic 98 may repeat the method 110 for each switch 86, 88, 90 in the display driver IC 58 to determine the resistance of each conductive layer coupled to the display driver IC 58. By measuring the resistance of the TFT layer 59, the control logic 98 may obtain information related to the features of the display 12. This information may enable the manufacturers of the display 12 to better assess the quality of the display 12 after being manufactured. For instance, FIG. 7 illustrates a method 140 for assessing the quality of a display 12. Referring to FIG. 7, at block 142, an LCD panel may be manufactured. In one embodiment, the LCD panel may be manufactured with a display driver IC 58 as described above.

At block 144, the resistance of the TFT layer 59 (i.e., sheet resistance) in the LCD panel may be measured. As such, a test circuit 28, as described above, may be coupled to the display driver IC 58 via the FOG circuit 54. The control logic 98 of the test circuit 28 may then measure the resistances of the TFT layer 59 in the LCD panel using a process similar to the method 110 of FIG. 6.

If the measured sheet resistance of the TFT layer 59 are within some limits (block 146), the LCD panel may pass a quality assurance test for the manufacturing of the LCD panel (block 148). If, however, the measured sheet resistance of the TFT layer 59 are not within some limits (block 146), the LCD panel may not pass the quality assurance test for the manufacturing of the LCD panel (block 150).

Although the method 140 has been described as being performed after manufacturing the LCD panel, it should be noted that, in some embodiments, the method 130 may be performed at any time after the LCD panel has been manufactured. In other words, the quality of the LCD panel may be assessed over time by measuring the resistance of the TFT layer 59 over time. For example, the test circuit 28 may be invoked by the processor 18 after the LCD panel has been integrated into any electronic devices such as those described above with reference to FIGS. 2-3.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A display driver integrated circuit (IC) for determining a sheet resistance of a display panel, comprising:
    a first switch coupled to a first input/output (I/O) pad and a second I/O pad, wherein the first I/O pad is configured to couple to a voltage source and the second I/O pad is configured to couple to a current source; and
    a second switch coupled to a third I/O pad and the second I/O pad, wherein the second switch has substantially the same geometry as the first switch, and wherein the third I/O pad is configured to couple to a thin-film transistor (TFT) layer of the display panel.

2. The display driver IC of claim 1, wherein the first switch and the second switch are metal-oxide-semiconductor field-effect transistor (MOSFET) switches.

3. The display driver IC of claim 1, wherein the second I/O pad is coupled to the current source via a flex-on-glass (FOG) circuit.

4. The display driver IC of claim 1, wherein the current source comprises a direct current (DC) source.

5. The display driver IC of claim 1, comprising a plurality of I/O pads configured to couple to a plurality of conductive layers coupled to the display driver IC.

6. The display driver IC of claim 5, wherein each of the plurality of conductive layers is different.

7. A system, comprising:
    a display driver integrated circuit (IC), comprising:
        a first switch coupled to a first input/output (I/O) pad and a second I/O pad, wherein the first I/O pad is coupled to a voltage source, and wherein the second I/O pad is coupled to a current source; and
        a second switch coupled to a third I/O pad and the second I/O pad, wherein the third I/O pad is coupled to a thin-film transistor (TFT) layer of a liquid crystal display (LCD); and
    a test circuit, comprising:
        the current source; and
        a controller configured to determine a resistance of the TFT layer by controlling the first switch, the second switch, and the current source.

8. The system of claim 7, wherein the controller is configured to determine the resistance of the TFT layer by:
    measuring a first voltage at the second I/O pad when the first switch is closed;
    measuring a second voltage at the second I/O pad when the first switch is closed and a first current is provided to the first switch via the current source;
    determining a resistance of the first switch based at least in part on the first voltage, the second voltage, and the first current;
    providing a second current from the current source to the second I/O pad when the first switch is open and the second switch is closed, wherein the second current is configured to bias the second switch such that a resistance of the second switch is substantially the same as the resistance of the first switch; and
    determining the resistance of the TFT layer based at least in part on the second current and the resistance of the first switch.

9. The system of claim 8, wherein the first voltage and the second voltage are floating voltages.

10. The system of claim 8, wherein the resistance of the first switch is determined according to:

$$R_{path}=(V'_i-V_i)/I_{test}$$

where $R_{path}$ is the resistance of the first switch, $V_i$ is the first voltage, $V'_i$ is the second voltage, and $I_{test}$ is the first current.

11. The system of claim 8, wherein providing the second current from the current source to the second I/O pad comprises sweeping the current source until a third voltage at the second I/O pad is substantially equal to the second voltage.

12. The system of claim 11, wherein the resistance of the TFT layer is determined according to:

$$R_x=(V_x-I_{test\_x}*R_{path})/I_{test\_x}$$

where $R_x$ is the resistance of the TFT layer, $V_x$ is the third voltage, and $I_{test\_x}$ is the second current.

13. An electronic device, comprising:
    a display comprising a chip-on-glass (COG) circuit and a flex-on-glass circuit (FOG), wherein the display is configured to display image data, and wherein the COG circuit comprises:
        a first switch coupled to a first COG pad and a second COG pad disposed on the COG circuit, wherein the first COG pad is coupled to a voltage source the second COG pad is coupled to a FOG pad disposed on the FOG circuit; and
        a second switch coupled to a third COG pad and the second COG pad, wherein the third COG pad is coupled to a thin-film transistor (TFT) layer of the display; and
    a test circuit comprising a current source, wherein the test circuit is configured to couple the current source to the FOG pad.

14. The electronic device of claim 13, wherein the test circuit is configured to couple to the COG circuit and control operations of the first switch and the second switch.

15. The electronic device of claim 13, comprising a processor configured to couple to the test circuit and to the COG circuit, and wherein the processor is configured to determine a resistance of the TFT layer by:
    measuring a first voltage at the FOG pad when the first switch is closed;
    measuring a second voltage at the FOG pad when the first switch is closed and a first current is provided to the first switch via the current source;

determining a resistance of the first switch based at least in part on the first voltage, the second voltage, and the first current;

providing a second current from the current source to the FOG pad when the first switch is open and the second switch is closed, wherein the second current corresponds to when a voltage at the FOG pad is substantially equal to the second voltage; and determining the resistance of the TFT layer based at least in part on the second current, the second voltage, and the resistance of the first switch.

16. The electronic device of claim 15, wherein the processor is configured to determine the resistance of the TFT layer at one or more times.

17. A liquid crystal display (LCD), comprising:
a test circuit comprising a current source;
a display driver integrated circuit (IC), comprising:
  a first switch coupled to a first input/output (I/O) pad and a second I/O pad, wherein the first I/O pad is coupled to a voltage source, and wherein the second I/O pad is coupled to the current source; and
  a second switch coupled to a third I/O pad and the second I/O pad, wherein the third I/O pad is coupled to a thin-film transistor (TFT) layer of the LCD; and
a controller configured to determine a resistance of the TFT layer by:
  determining a resistance of the first switch based at least in part on a first current provided by the current source, a plurality of voltage values that correspond to when the first switch is closed and the current source is off and when the first switch is closed and the current source is on, and a first current provided by the current source when the first switch is closed and the current source is on; and
  determining the resistance of the TFT layer based at least in part on the resistance of the first switch, a first voltage at the second I/O pad when the second switch is closed, and a second current provided by the current source.

18. The LCD of claim 17, wherein the second current is configured such that the first voltage is substantially the same as a second voltage at the second I/O pad that corresponds to when the first switch is closed and the current source is providing the first current.

19. A method for determining a quality of a display, comprising:
determining a resistance of a thin-film transistor (TFT) layer of the display by:
  measuring a first voltage at a first I/O pad when a first switch coupled between the first I/O pad and a voltage source is closed;
  measuring a second voltage at the first I/O pad when the first switch is closed and a first current is provided to the first switch via a current source;
  determining a resistance of the first switch based at least in part on the first voltage, the second voltage, and the first current;
  providing a second current from the current source to the first I/O pad when the first switch is open and a second switch is closed, wherein the second switch is coupled between the first I/O pad and the TFT layer, wherein the second current is configured to bias the second switch such that a resistance of the second switch is substantially the same as the resistance of the first switch; and
  determining the resistance of the TFT layer based at least in part on the second current and the resistance of the first switch;
determining whether the resistance of the TFT layer is within limits; and
determining that the display has failed a quality assurance test when the resistance of the TFT layer is not within the limits.

20. The method of claim 19, comprising determining the quality of the display based at least in part on a plurality of measured resistances of the TFT layer over a period of time.

* * * * *